(12) United States Patent
Ren et al.

(10) Patent No.: US 10,973,585 B2
(45) Date of Patent: Apr. 13, 2021

(54) SYSTEMS AND METHODS FOR TRACKING THE ORIENTATION OF SURGICAL TOOLS

(71) Applicant: Novartis AG, Basel (CH)

(72) Inventors: Hugang Ren, Cypress, CA (US); Lingfeng Yu, Rancho Santa Margarita, CA (US)

(73) Assignee: Alcon Inc.

( * ) Notice: Subject to any disclaimer, the term of this patent is extended or adjusted under 35 U.S.C. 154(b) by 349 days.

(21) Appl. No.: 15/271,833

(22) Filed: Sep. 21, 2016

(65) Prior Publication Data

US 2018/0078315 A1 Mar. 22, 2018

(51) Int. Cl.
*A61B 34/20* (2016.01)
*A61B 3/10* (2006.01)
*A61F 9/007* (2006.01)
*A61B 90/00* (2016.01)
*A61F 9/008* (2006.01)
*A61B 90/30* (2016.01)

(52) U.S. Cl.
CPC .............. *A61B 34/20* (2016.02); *A61B 3/102* (2013.01); *A61B 3/1025* (2013.01); *A61F 9/007* (2013.01); *A61F 9/00736* (2013.01); *A61B 90/30* (2016.02); *A61B 90/361* (2016.02); *A61B 2034/2065* (2016.02); *A61B 2090/3735* (2016.02); *A61B 2090/3937* (2016.02); *A61B 2090/3979* (2016.02); *A61F 2009/00851* (2013.01); *A61F 2009/00876* (2013.01)

(58) Field of Classification Search
CPC .......... A61B 34/20; A61B 90/13; A61B 3/102; A61B 3/1025; A61B 5/0066; A61F 9/007; A61F 9/00736
See application file for complete search history.

(56) References Cited

U.S. PATENT DOCUMENTS 5,867,308 A 2/1999 Pensel et al.
6,153,836 A * 11/2000 Goszyk ................ G01B 11/002
178/19.01

(Continued)

FOREIGN PATENT DOCUMENTS

CN 101052434 A 10/2007
CN 102341054 A 2/2012

(Continued)

OTHER PUBLICATIONS

International Search Report and Written Opinion issued for PCT/US2014/068899, dated Mar. 5, 2015, 8 pgs.

(Continued)

*Primary Examiner* — Bill Thomson
*Assistant Examiner* — Younhee Choi (57) ABSTRACT

Some embodiments of the present technology involve methods, devices, and systems for determining an orientation of a surgical tool during ophthalmic surgery. An example method includes performing an optical imaging scan in the surgical site, using a scan pattern that intersects the surgical tool and generating a scan image from the optical imaging scan. The example method further comprises analyzing the scan image to determine a location in the scan image corresponding to where the surgical tool intersected the optical imaging scan, and determining an orientation of the surgical tool, based on the determined location.

22 Claims, 7 Drawing Sheets

(56) References Cited

U.S. PATENT DOCUMENTS

| | | | |
|---|---|---|---|
| 6,995,762 B1* | 2/2006 | Pavlidis | G06T 17/00 345/419 |
| 7,493,153 B2 | 2/2009 | Ahmed et al. | |
| 8,108,190 B2 | 1/2012 | Riener et al. | |
| 8,170,698 B1 | 5/2012 | Gusack | |
| 9,129,054 B2 | 9/2015 | Nawana et al. | |
| 9,733,463 B2* | 8/2017 | Eslami | G02B 21/22 |
| 10,182,714 B2* | 1/2019 | Eslami | A61B 5/0035 |
| 2003/0169603 A1 | 9/2003 | Luloh et al. | |
| 2004/0102729 A1 | 5/2004 | Haffner et al. | |
| 2004/0111183 A1 | 6/2004 | Sutherland et al. | |
| 2004/0254454 A1 | 12/2004 | Kockro | |
| 2005/0015005 A1 | 1/2005 | Kockro | |
| 2005/0203367 A1 | 9/2005 | Ahmed et al. | |
| 2007/0032906 A1 | 2/2007 | Sutherland et al. | |
| 2007/0236514 A1 | 10/2007 | Agusanto et al. | |
| 2007/0238981 A1 | 10/2007 | Zhu et al. | |
| 2007/0291277 A1* | 12/2007 | Everett | A61B 3/102 356/497 |
| 2008/0058704 A1* | 3/2008 | Hee | A61F 9/0017 604/21 |
| 2008/0161830 A1 | 7/2008 | Sutherland et al. | |
| 2008/0297535 A1 | 12/2008 | Reinig | |
| 2009/0182312 A1 | 7/2009 | Gertner et al. | |
| 2010/0063630 A1 | 3/2010 | Sutherland et al. | |
| 2010/0168763 A1 | 7/2010 | Zhao et al. | |
| 2010/0208202 A1 | 8/2010 | Itoh et al. | |
| 2010/0228119 A1 | 9/2010 | Brennan et al. | |
| 2010/0228249 A1 | 9/2010 | Mohr et al. | |
| 2011/0282331 A1 | 11/2011 | Brennan et al. | |
| 2012/0059378 A1 | 3/2012 | Farrell | |
| 2012/0071891 A1 | 3/2012 | Itkowitz et al. | |
| 2012/0184846 A1* | 7/2012 | Izatt | A61B 3/132 600/425 |
| 2013/0038836 A1 | 2/2013 | Smith | |
| 2013/0217967 A1 | 8/2013 | Mohr et al. | |
| 2013/0245375 A1 | 9/2013 | Dimaio et al. | |
| 2013/0281817 A1 | 10/2013 | Schaller et al. | |
| 2014/0005484 A1 | 1/2014 | Charles | |
| 2014/0005485 A1 | 1/2014 | Tesar et al. | |
| 2014/0005486 A1 | 1/2014 | Charles | |
| 2014/0005487 A1 | 1/2014 | Tesar | |
| 2014/0005488 A1 | 1/2014 | Charles et al. | |
| 2014/0005489 A1 | 1/2014 | Charles | |
| 2014/0005555 A1 | 1/2014 | Tesar | |
| 2014/0081659 A1 | 3/2014 | Nawana et al. | |
| 2014/0088941 A1 | 3/2014 | Banerjee et al. | |
| 2014/0088990 A1 | 3/2014 | Nawana et al. | |
| 2014/0094968 A1 | 4/2014 | Taylor et al. | |
| 2014/0315174 A1 | 10/2014 | Sassani et al. | |
| 2014/0316388 A1 | 10/2014 | Hipsley | |
| 2015/0007033 A1 | 1/2015 | Kiey et al. | |
| 2015/0018622 A1 | 1/2015 | Tesar et al. | |
| 2015/0085095 A1 | 3/2015 | Tesar | |
| 2015/0141759 A1 | 5/2015 | Charles et al. | |
| 2015/0173644 A1 | 6/2015 | Ren et al. | |
| 2015/0238073 A1 | 8/2015 | Charles et al. | |
| 2015/0261922 A1 | 9/2015 | Nawana et al. | |
| 2015/0272694 A1 | 10/2015 | Charles | |
| 2015/0282796 A1 | 10/2015 | Nawana et al. | |
| 2015/0297311 A1 | 10/2015 | Tesar | |
| 2016/0100908 A1 | 4/2016 | Tesar | |
| 2016/0216882 A1 | 7/2016 | Kiey et al. | |
| 2016/0270656 A1 | 9/2016 | Samec et al. | |
| 2016/0338685 A1 | 11/2016 | Nawana et al. | |
| 2017/0276926 A1* | 9/2017 | Ootsuki | G02B 21/367 |
| 2018/0235457 A1* | 8/2018 | Kagemann, Jr. | A61F 9/00781 |

FOREIGN PATENT DOCUMENTS

| | | | |
|---|---|---|---|
| DE | 102004049258 A1 | 4/2006 | |
| JP | 09-149876 A | 10/1997 | |
| JP | 10-118076 A | 12/1998 | |
| JP | 2007-535382 A | 12/2007 | |
| JP | 4095044 B | 6/2008 | |
| JP | 2009-201682 A | 10/2009 | |
| JP | 2012-506272 | 3/2012 | |
| WO | 2005107845 | 11/2005 | |
| WO | 2011085815 A1 | 7/2011 | |
| WO | 2014170236 A1 | 10/2014 | |
| WO | WO 2017195192 A1 * | 11/2017 | A61B 3/14 |

OTHER PUBLICATIONS

International Searching Authority, International Search Report, PCT/US2016/019146, dated May 12, 2016, 7 pages.

International Searching Authority, Written Opinion, PCT/US2016/019146, dated May 12, 2016, 7 pages.

Richa, Rogerio et al, Vision-Based Proximity Detection in Retinal Surgery, IEEE Transactions on Biomedical Engineering, vol. 59, No. 8, Aug. 2012, pp. 2291-2301, © Springer-Verlag Berlin Heidelberg 2012.

Sznitman, Raphael et al, Data-Driven Visual Tracking in Retinal Microsurgery, MICCAI 2012, Part II, LNCS 7511, pp. 568-575, 2012.

Sznitman, Raphael et al, Unified Detection and Tracking in Retinal Microsurgery, MICCAI 2011, Part I, LNCS 6891, pp. 1-8, 2011 © Springer-Verlag Berlin Heidelberg 2011.

* cited by examiner

SYSTEMS AND METHODS FOR TRACKING THE ORIENTATION OF SURGICAL TOOLS

TECHNICAL FIELD

The devices, systems, and methods disclosed herein relate generally to automatic tracking of surgical tools, and more particularly to the automatic tracking of surgical tools during ophthalmic surgeries.

BACKGROUND

Surgical tools, such as surgical imaging probes, surgical forceps, surgical scissors, surgical vitrectomy probes, and the like, may be inserted into an eye during an ophthalmic surgery to perform various surgeries in the eye. Typically, a distal portion of a surgical tool is inserted into the eye during the ophthalmic surgery. Thus, the area of the eye surrounding the distal tip of the surgical tool is a region of interest to a surgeon. To achieve guided surgical interventions, such as intra-operative Optical Coherence Tomography (OCT) for Internal Limited Membrane (ILM) peeling, automatic tool tip tracking is used to efficiently close a feedback loop to allow the OCT engine to locate the scanning target area. Further, to provide real time feedback during surgery, useful surgical data may be overlaid to the surgeon's current area of interest. When a surgeon moves the distal portion of the surgical tool inserted into the eye, the area of interest may shift accordingly. Thus, automatic tool tracking may be used to locate the area of interest to adjust the surgical data overlay so the surgeon may visualize it without looking away from the current area of interest.

There are three conventional techniques for general object tracking. A first technique is motion-based object tracking. Motion-based object tracking may be used for automated surveillance. Motion-based object tracking may use image processing algorithms, such as background subtraction, frame difference, and optical flow, to track an object. Nevertheless, motion-based object tracking algorithm requires a quasi-stationary background, and may not be suitable for tool tracking in an ophthalmic surgery in which background may vary constantly.

A second technique for general object tracking is region-based object tracking. Region-based object tracking may be used for tracking simple objects. In region-based object tracking, an object template is preselected offline or during a first frame. For the subsequent frames, the template is searched across the whole field of view and the location with the greatest similarity to the template is identified as the object. Region-based object tracking is sensitive to object pose variations and local illumination changes, however, and may not be suitable for tool tracking in an ophthalmic surgery, in which illumination and orientation of the tool vary greatly.

A third technique for general object tracking is feature-based object tracking. Feature-based object tracking may extract and search for unique features of an object, such as contour, edge, shape, color, corner/interest point and the like, across the entire field of view for object detection. In a feature-based tracking algorithm, a high contrast feature, which is not sensitive to environmental and object pose changes and is unique to the object, is required. Since most surgical tools do not intrinsically possess high-contrast features, feature based object tracking may not provide suitable results.

In a vitreo-retinal surgery, illumination conditions may be challenging for tool tracking. An endo illuminator may be inserted into the eye for illumination. Because the endo illuminator may move during a surgery, the illumination condition may vary greatly from image frame to image frame and the images of the fundus area being illuminated may change greatly over time. Motion-based and region-based object tracking techniques may be difficult to implement under inconsistent illumination conditions. Further, with a single illuminator illuminating from one side, shadow artifacts and specular reflection from the surgical tool may increase complexity for tool tracking. Moreover, in order to capture a fundus image through a video camera, a beam path of an imaging light from the eye may pass through multiple optical elements and media, such as eye vitreous body, an aged crystalline lens, eye cornea, and Binocular Indirect Ophthalmomicroscope (BIOM) lenses. These optical elements in the beam path of imaging light may further degrade the image quality and reduce contrast. Thus, it may be difficult to extract an intrinsic feature of various surgical tools to achieve real time tool tracking.

The present disclosure is directed to devices, systems, and methods for the automatic tracking of surgical tools, which address one or more disadvantages of the prior art.

SUMMARY

Methods, devices, and systems for determining an orientation of a surgical tool during ophthalmic surgery are disclosed. An example method includes performing an optical imaging scan in the surgical site, using a scan pattern that intersects the surgical tool and generating a scan image from the optical imaging scan. The example method further comprises analyzing the scan image to determine a location in the scan image corresponding to where the surgical tool intersected the optical imaging scan, and determining an orientation of the surgical tool, based on the determined location.

A corresponding system for determining an orientation of a surgical tool during ophthalmic surgery comprises an optical imaging apparatus configured to perform optical imaging scans in the surgical site, the optical imaging apparatus in turn comprising a light source configured to introduce an imaging light into the surgical site, and an imaging device configured to receive imaging light reflected from the surgical site and to generate a scan image from each optical imaging scan. The system further comprises a controller operatively coupled to the optical imaging apparatus and configured to control the optical imaging apparatus to perform an optical imaging scan using a scan pattern configured to intersect the surgical tool and to generate a scan image from the optical imaging scan. The controller is further configured to analyze the scan image to determine a location in the scan image corresponding to where the surgical tool intersected the optical imaging scan, and to determine an orientation of the surgical tool, based on the determined location.

It is to be understood that both the foregoing general description and the following detailed description are exemplary and explanatory in nature, and are intended to provide an understanding of the presently disclosed techniques and apparatus without limiting the scope of those techniques and apparatus. In that regard, additional aspects, features, and advantages of the presently disclosed techniques and apparatus will be apparent to those skilled in the art from the following detailed description and the accompanying figures.

BRIEF DESCRIPTION OF THE FIGURES

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

Intra-operative OCT is an emerging technology that can provide high resolution depth resolved tissue structural and functional information during surgery in real time. Therefore, using intra-operative OCT to guide delicate surgery, such as ophthalmic surgery, is gaining popularity in both research facilities and hospital operating rooms.

In order to obtain useful intra-operative OCT information to guide the surgery, it is critical for the surgeon to be able to direct the OCT scan to the desired location of interest. To achieve this, in commercially available intra-operative OCT systems, a foot pedal is used to manually move the OCT beam during the surgery. This, however, not only adds quite amount of extra work to the already busy surgical workflow, but also lacks accuracy for the placement of the OCT scan.

A previous disclosure by the present inventors, U.S. patent application Ser. No. 14/134,237, filed 19 Dec. 2013 and published as U.S. Patent Application Publication 2015/0173644, described techniques and apparatus for tracking the tip of the surgical tool to automatically direct the OCT scan to the desired location. This and related approaches empower the surgeon to have control of the OCT scan by moving the tip of the surgical tool. For the purposes of providing background to the detailed discussion, the entire contents of U.S. Patent Application Publication 2015/0173644 are incorporated herein by reference.

In short, guided surgical interventions in the context of ophthalmic surgery may use intra-operative Optical Coherence Tomography (OCT), where automatic tool tip tracking is used to close a feedback loop that allows the OCT engine to locate the scanning target area. In addition to the problems discussed above for conventional object-tracking techniques, a problem that arises in the context of intra-operative OCT is that a tracked surgical tool will have a shadowing effect and, depending on its orientation, may partially block the OCT beam, even if the tip of the tool has been accurately tracked. For the OCT to be most useful, it is important to have the OCT beam scan at a preferred angle, where the tool shadow occupies as little as possible of the OCT image.

Moreover, the surgeon may want to examine several features simultaneously within one OCT scan, while those features could be distributed along an arbitrary angle. When using OCT line scan based on tracking only the tip of the surgical tool, it is impossible to automatically avoid the tool shadow while imaging multiple features at any arbitrary angle.

To address these problems, the techniques, devices, and systems disclosed herein provide for the tracking of a surgical tool's orientation, using OCT. Using this orientation information, a smart OCT scan be designed, so that tool shadow is avoided all or most of the time. Further, by simply changing the orientation of the surgical tool, the surgeon can control the OCT beam—this provides another degree of freedom in the surgeon's control of the system, providing for the simultaneous imaging of multiple features at any arbitrary angle.

Figure 1:
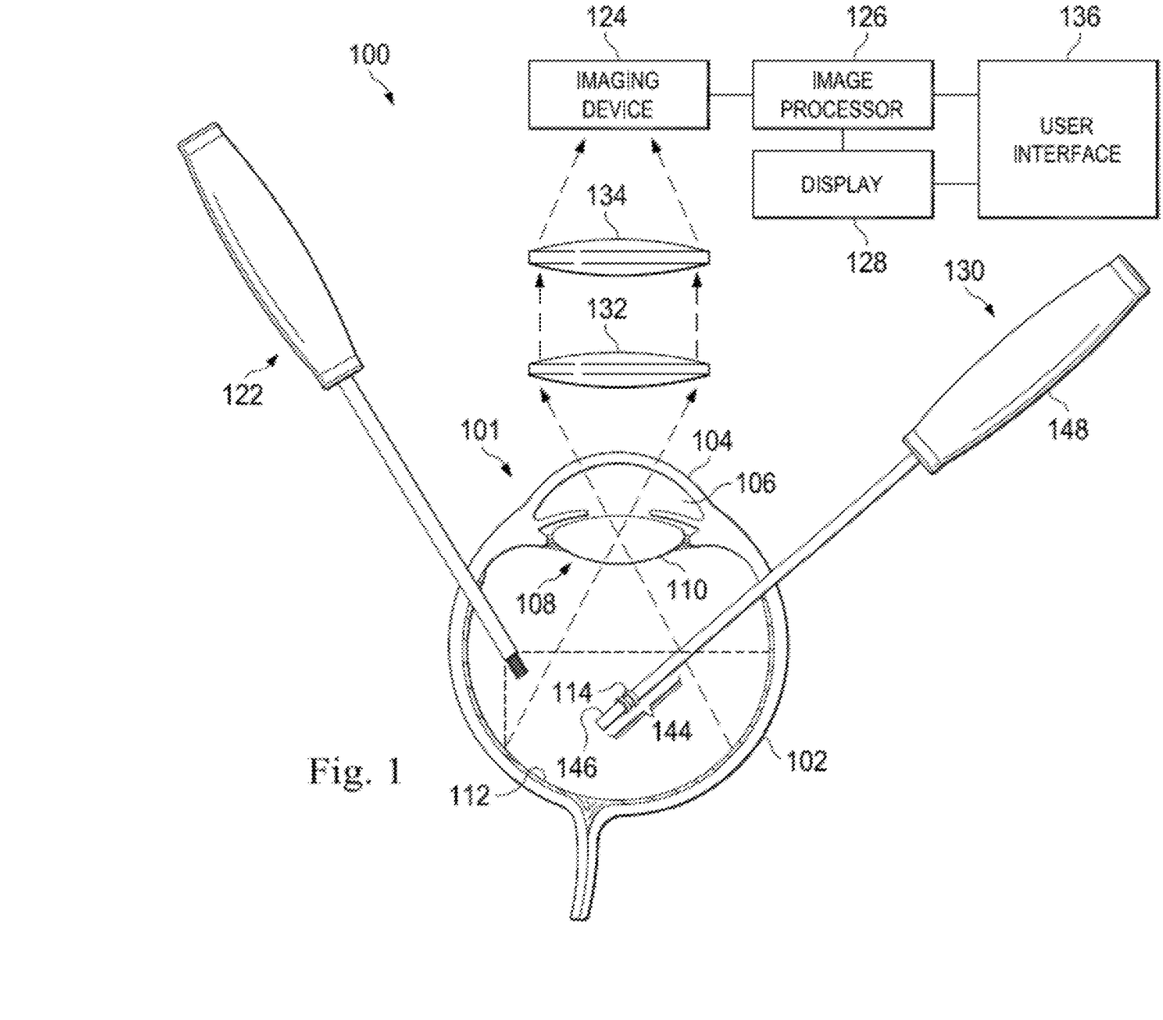
FIG. 1 illustrates a schematic diagram of an exemplary ophthalmic surgical tool tracking system.

To provide a technical context for the detailed description of the invention that follows, FIG. 1 illustrates an exemplary ophthalmic surgical tool tracking system, generally designated 100, disposed relative to an eye 101 under treatment. The eye 101 includes sclera 102, a cornea 104, an anterior chamber 106, and a posterior chamber 108. A capsular bag 110 is illustrated in the posterior chamber 108. The eye 101 further includes a retina 112. An ophthalmic surgical tool 130 may be used to perform surgery in the eye 101. The ophthalmic surgical tool 130 may be sized and shaped to be handled by a surgeon and to protrude into the eye 101 of the patient.

The ophthalmic surgical tool 130 may include a proximal portion 148 and a distal portion 144. The proximal portion 148 may be sized and shaped for handheld grasping by a user. For example, the proximal portion 148 may define a handle which is sized and shaped for grasping by a single hand of the user. In use, the user may control the position of the distal portion 144 by maneuvering the proximal portion 148. The distal portion 144 of the ophthalmic surgical tool 130 may include a marker 114. The marker may have a high contrast feature in the visible light or infrared spectrum or other spectral ranges detectable by an imaging device 124 of the ophthalmic surgical tool tracking system 100.

The ophthalmic surgical tool tracking system 100 also may include a light source 122, e.g., an endo illuminator. The light source 122 may have a distal portion that is configured to be inserted into the eye 101. A distal tip of the light source 122 may emit an imaging light that may illuminate a fundus of the eye 101. The fundus is an interior surface of the eye 101 and may include the retina 112. The imaging light from the light source 122 may be reflected from the fundus and the distal portion 144 of the ophthalmic surgical tool 130. The reflected imaging light may pass through the capsular bag 110, the anterior chamber 106, the cornea 104, and be received by the imaging device 124, which is configured to capture fundus images of the eye 101. Lenses 132 and 134 may be provided between the eye 101 and the imaging device 124 to receive the reflected imaging light from the fundus and direct the imaging light to the imaging device 124.

In some embodiments, the imaging device 124 may include one or more video cameras configured to capture images of the fundus. The video camera may capture images in visible light spectrum, infrared spectrum or other spectral ranges. For example, imaging device 124 may include either or both a video camera that captures images of the fundus in visible light spectrum and a video camera that captures infrared images of an infrared marker 114 near the fundus in the infrared spectrum.

The ophthalmic surgical tool tracking system 100 also may include an image processor 126. The image processor 126 may receive image frames captured by the imaging device 124 and perform various image processing on the image frames. In particular, the image processor 126 may perform image analysis on the image frames to identify and extract the image of the marker 114 from the image frames. Further, the image processor 126 may generate indicators and overlay the indicators on the image of the fundus or a processed image. The indicators may include surgical data, such as the position and orientation of the marker 114 in the image of the fundus, the position and orientation of a distal tip 146 of the ophthalmic surgical tool 130, an image, a surgical setting parameter. The overlaid image may then be displayed by a display 128 to the user.

The imaging device 124, the image processor 126, and the display 128 may be implemented in separate housings communicatively coupled to one another or within a common console or housing. A user interface 136 may be associated with the display 128 and/or the image processor 126. It may include, for example, a keyboard, a mouse, a joystick, a touchscreen, an eye tracking device, a speech recognition device, a gesture control module, dials, and/or buttons, among other input devices. A user may enter desired instructions or parameters at the user interface 136 to control the imaging device 124 for taking images of the eye 101. During an ophthalmic surgery, a surgeon may review the images of the fundus and/or the overlaid indicators on the display 128 to visualize the operation and the relative position of the distal tip 146 of the ophthalmic surgical tool 130 within various portions of the fundus.

Figure 2:
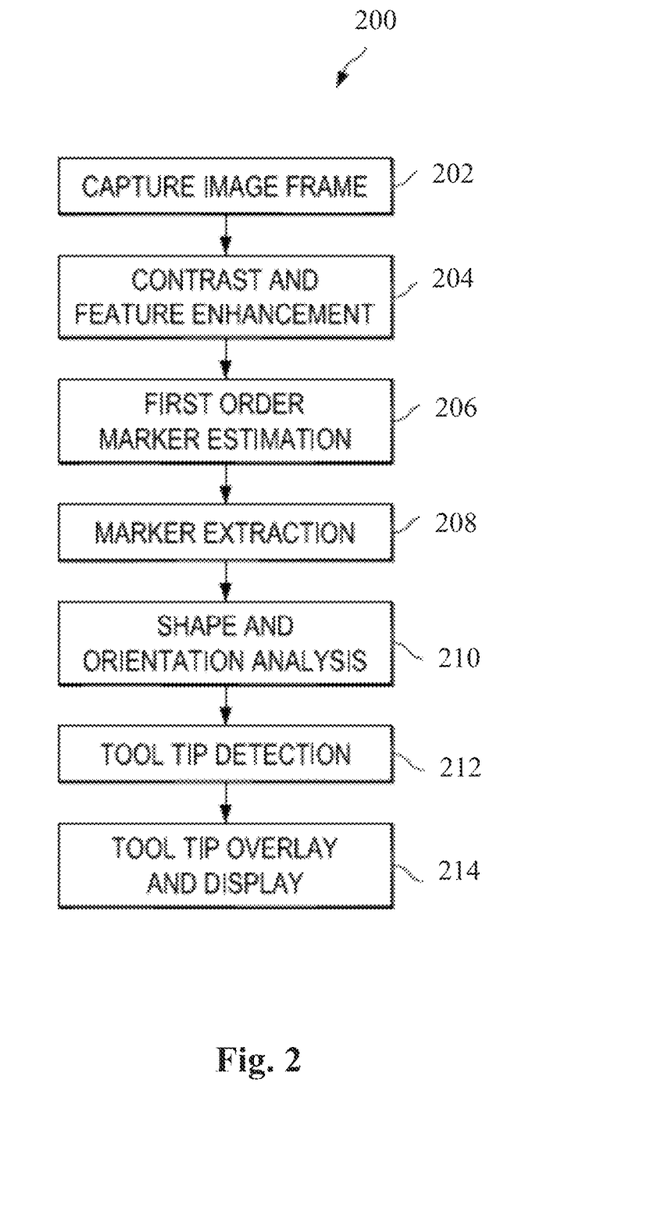
FIG. 2 is a flow chart illustrating a method for tracking the tip of a surgical tool.

FIG. 2 illustrates a chart illustrating an example method 200 for tracking the tip of an ophthalmic surgical tool 130 inserted in an eye 101. As noted above, a light source 122 may introduce imaging light into the fundus of the eye 101. The reflected imaging light from the fundus may be guided by lenses 132 and 134 and received by imaging device 124. At 202, the imaging device 124 captures images of the fundus. In particular, the imaging device 124 may capture frames of images to form a video. Each image frame may be forwarded to the image processor 126 to be processed and analyzed.

At 204, the image processor 126 performs contrast and feature enhancement processing on the image frame. For example, the image processor 126 may receive the image frame in Red-Green-Blue (RGB) format. At 204, the image processor 126 may convert the RGB format image frame into a Hue-Saturation-Value (HSV) space. At 206, after the image frame has been enhanced to bring out the contrast and feature, the image processor 126 determines a first-order estimation mask of the marker 114. For example, based on a predetermined color of the marker 114, the image processor 126 may apply criteria to the hue and saturation channels of the HSV image frame that may separate the marker 114 from the background in order to bring out and estimate the image of the marker 114.

At 208, the image processor 126 extracts the image of the marker 114 from the image frame. For example, the image processor 126 may implement a blob detection process to detect a boundary of the marker 114 in the image frame. A blob may be a region of the image frame where some properties, such as color and brightness, are approximately constant. The image processor 126 may search for regions of approximately constant properties in the image frame to detect blobs. Thus, the image processor 126 may find the boundary of the marker 114 and extract the marker 114 from the image frame.

At 210, the image processor 126 analyzes the shape of the marker 114 extracted from the image frame. Depending on the shape and/or pattern and color of the marker 114, the image processor 126 may be able to determine the orientation of the marker 114 in the image frame. For example, if the marker 114 has stripes, the image processor 126 may determine the orientation of the marker 114 based on the orientation and direction of the stripes.

At 212, the image processor 126 determines the position of the distal tip 146 of the ophthalmic surgical tool 130. If the orientation of the marker 114 is discernable, the image processor 126 may also determine the orientation of the tool's distal tip 146. In particular, based on the position and orientation of the marker 114, the image processor 126 may determine the position and orientation of the distal tip 146 of the ophthalmic surgical tool 130. For example, the marker 114 may be positioned from the distal tip 146 of the ophthalmic surgical tool 130 by a predetermined distance and may have a pattern that indicates a pointing direction of the ophthalmic surgical tool 130, e.g., a strip or an arrow. Thus, based on the position and the pattern of the marker 114, the image processor 126 may determine the position of the distal tip 146 of the ophthalmic surgical tool and the pointing direction or orientation of the ophthalmic surgical tool.

At 214, the image processor 126 may display and overlay indicators to indicate the distal tip 146 of the ophthalmic surgical tool 130 or other surgical data for surgical guidance. For example, the image processor 126 may generate an indicator, such as a box, a circle, a star, or an arrow, and overlay the indicator into the image frame at the position of the distal tip 146 of the ophthalmic surgical tool 130. Further, the indicator may indicate an orientation, e.g., a pointing angle, of the ophthalmic surgical tool 130. For example, an arrow may be used as the indicator to indicate the pointing direction of the ophthalmic surgical tool 130. Further, the indicator may also include an image, such as an OCT image of a region of the retina 112, or a surgical setting parameter, such as a cutting speed of a vitrectomy probe. The display 128 may display the image frame overlaid with the indicators.

Further details of exemplary image processing and display processing, applicable to the method shown in FIG. 2, are provided in U.S. Patent Application 2015/0173644, which was incorporated by reference into the present disclosure, above.

Figure 3:
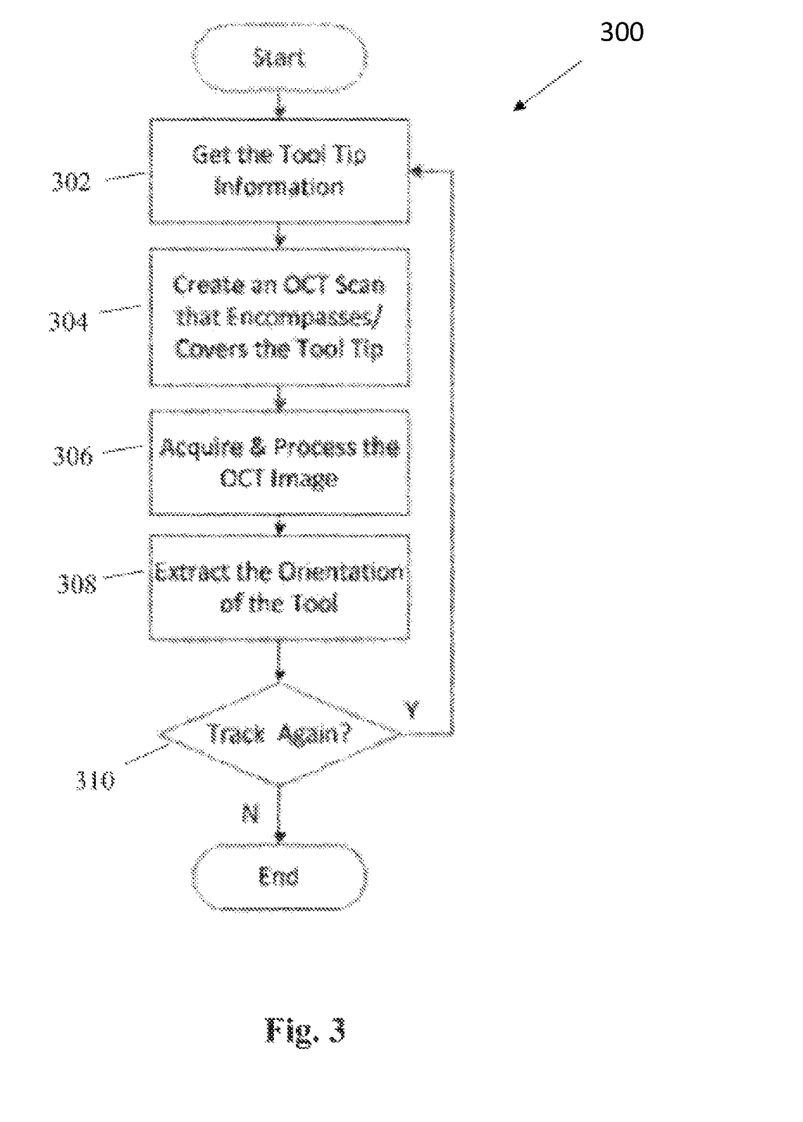
FIG. 3 is a flow chart illustrating an example method for tracking the orientation of a surgical tool.

FIG. 3 is a flow chart illustrating an example method 300 for tracking the orientation of the surgical tool during an ophthalmic surgery using intra-operative OCT. It will be appreciated that while the marking-based procedure described above may, at least in some circumstances, provide an indication as to the orientation of the distal tip of the surgical tool, the techniques described herein and illustrated generally in FIG. 3 may be used to determine a more complete and more accurate indication of the orientation of the remainder of the tool, e.g., the tool's shaft. Further, the techniques described herein, e.g., as illustrated in FIG. 3, may be used to determine the orientation of the surgical tool even when the orientation of a marking on the tool's tip cannot be discerned, e.g., because of the particular surgical conditions or even because the marking has no discernable orientation to begin with.

As seen in FIG. 3, the illustrated method begins, as shown at block 302, with obtaining the tool tip information, i.e., the position and, optionally, the orientation of the tool's distal end. This may be done, for example, using the technique illustrated in FIG. 2, as described above. However, other techniques for tracking the tool tip's position may be used, in some embodiments.

As shown at block 304, the method continues with the performing of an OCT scan that encompasses or covers, i.e., surrounds, the tool tip. Here, the OCT scan tracks a shape in a plane, or covers a region with multiple line scans, like a raster scan, for example, such that the tool's tip or a projection of the tool's tip onto that plane falls within that shape or region. As shown at block 306, the method continues with the acquisition and processing of the OCT image. This is followed, as shown at block 308, by the extracting of the tool's orientation, based on analyzing the OCT image to detect the intersection of the tool with the OCT scan. This can be repeated, as indicated at block 310, to track the tool's orientation in real time.

Figure 4A:
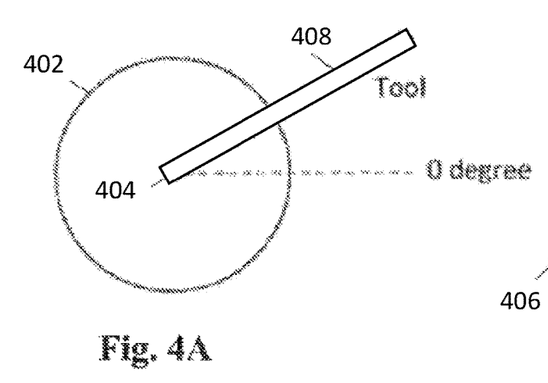
FIGS. 4A and 4B illustrate an example of tracking a tool's orientation using a circular OCT scan.
Figure 4B:
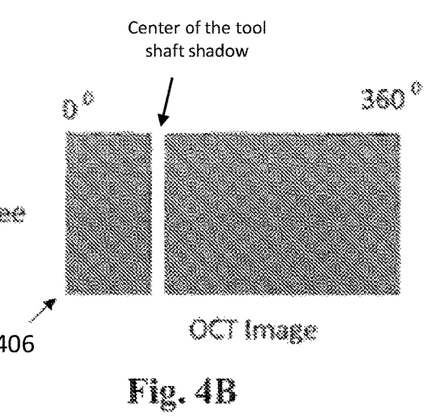

FIGS. 4A and 4B illustrate one example of tracking the orientation of the tool, where a circular scan around the tip of the tool is used. As seen in FIG. 4A, a circular scan pattern 402 around the tool tip 404 is created. FIG. 4B illustrates an example acquired OCT image 406, corresponding to the OCT scan pattern 402. Because the tool's shaft 408 will block the OCT beam during a portion of the scan, creating a shadowing effect, the location of the tool shaft's intersection with the OCT beam shows up in the OCT image as a prominent gap. Because this gap will generally have a high contrast to the surrounding image, the location of the center of the tool shaft can be reliably and accurately detected through OCT image processing. Given this location, and the previously determined position of the tool's tip, a precise orientation of the tool within the surgical field of view can be readily determined, e.g., with straightforward geometric calculations. With scans where the tip of the tool is known to be centered in the scan, the tool's orientation may be retrieved via a lookup table that indicates, for example, the angle associated with each vertical line in the scan image shown in FIG. 4B, relative to the scan's center point.

Figure 5A:
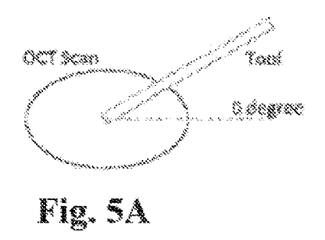
FIGS. 5A, 5B, 5C illustrate examples of other OCT scan shapes.
Figure 5B:
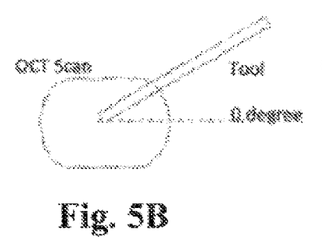
Figure 5C:
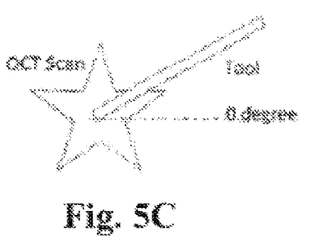

FIGS. 5A, 5B, and 5C illustrate other examples of scan patterns that may be used—it should be understand that any scan pattern that forms an at least substantially closed shape may be used. In other words, if a 360-degree range of angles is covered, relative to the position of the tool's tip in the plane of the scan, any closed-shape scan pattern can be used to track the orientation of the tool. FIG. 5A shows an example of elliptical, while FIG. 5B illustrates a round-corned rectangular scan. FIG. 5C shows a star shape scan pattern. It should be clear that the illustrated scan patterns are only examples; many other closed-shape patterns are possible.

Figure 6A:
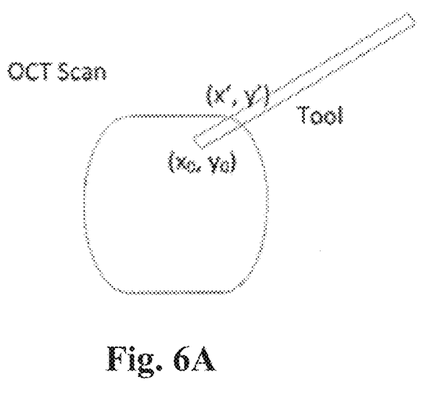
FIGS. 6A and 6B illustrate an example of tracking a tool's orientation when the tool tip is not at the center of the OCT scan.
Figure 6B:
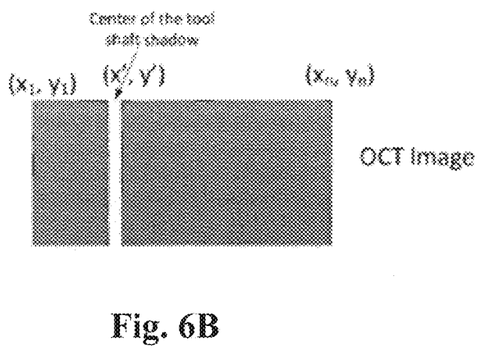

FIGS. 6A and 6B illustrate an example of tracking the surgical tool's orientation when the tool tip is not at the center of the closed-shape scan. As seen in FIG. 6B, the tool's tip is at a point (x0, y0) in the plane of the OCT scan, with the shaft of the tool intersecting the scan at the point (x', y'). In this case, the orientation of the tool cannot be directly extracted from the OCT image, e.g., via a look-up table. Instead, the coordinate (x', y') is determined from the OCT image, by determining the center of the shadow in the OCT image caused by the tool's shaft. Since the coordinate (x0, y0), which corresponds to the location of the tool's tip, is already known from the tool tip tracking process, the orientation of the line that includes (x0, y0) and (x', y') can be readily determined, giving the orientation of the tool within the surgical field of view.

Figure 7:
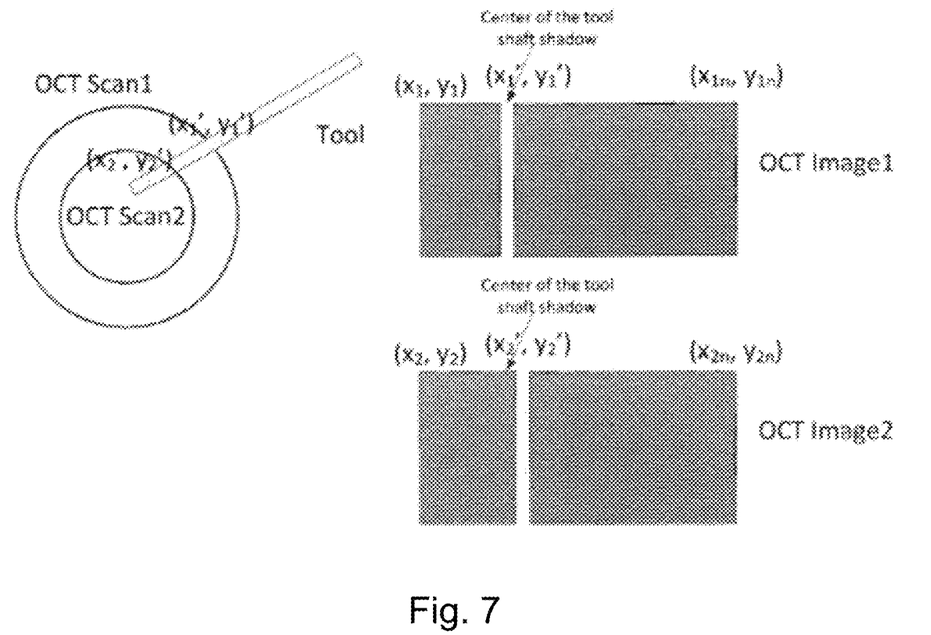
FIG. 7 illustrates an example of tracking a tool's orientation using a double-closed-shape OCT scan.

FIG. 7 illustrates an example where a double-closed-shape OCT scan pattern is used to track the orientation of the tool. In this case, a precise location of the tool tip does not need to be known. A double-closed-shape OCT may be performed, such that both of the closed OCT scans encompass (i.e., surround) an estimated location of the tool's tip. Two OCT scan images, as shown in the figure, are generated from the two closed-shape scan patterns. Assuming that the tool's tip falls inside both scan patterns, the tool will intersect both OCT scan images. The points at which the tool intersects the two scan patterns can be extracted directly from the two OCT scan images, as (x1', y1') and (x2', y2'). Given these two coordinates, the orientation of the tool within the surgical field of view can be readily calculated. Of course, it will be appreciated that more than two closed-shape scans can be used. This may be particularly useful, for example, when the shaft of the tool is not linear.

Figure 8:
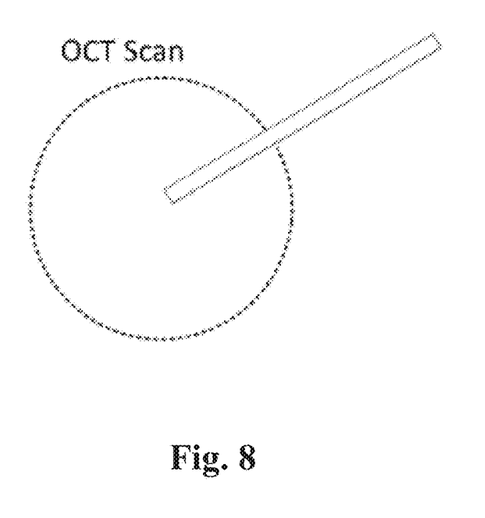
FIG. 8 shows an OCT scan pattern consisting of discrete points.

The patterns illustrated in FIGS. 4-7 and discussed above are simply examples of the many efficient OCT scan patterns that can be used to quickly and accurately determine the orientation of a surgical tool in the surgical field of view. Other scan patterns, such as a raster scan or other pattern of line scans covering a region around the tool tip may be used, so long as the pattern substantially encompasses or surround the tool tip. The scan pattern need not be continuous. A closed-shape scan may consist of discrete points, as shown in FIG. 8, so long as the spacing between the points is smaller than the surgical tool's lateral dimensions.

Furthermore, it should be noted that OCT is a three-dimensional imaging modality. This means that if a long-imaging-depth OCT scan is used, the location of the top surface of the tool may be discerned in the cross-sectional images. Adding this information to the two-dimensional orientation derived from the techniques described in connection with FIGS. 4-8, for example, allows the determination of the tool's orientation in three-dimensional space, in some embodiments.

Advantages of the techniques described above are that the orientation of a surgical tool within the surgical field of view can be reliably tracked. These techniques are not sensitive to focus change due to tool motion in the depth direction, since they rely primarily on the shadowing effect of the tool on the OCT image. Similarly, the angle of the tool may be quickly determined, in some cases directly from the OCT images. Because the shadow of the tool in the OCT image is typically very high contrast, the center of the tool can be accurately located, allowing for an accurate determination of the tool's angle, with respect to the scan plane. In some embodiments, the position of the tool with respect to the depth dimension of the scan can also be discerned, allowing for the determination of the tool's orientation in three-dimensional space.

Once the tool's orientation is determined, using the techniques described herein, this information can be fed back to the OCT control system, e.g., to change the angle of a subsequent line scan so as to avoid shadowing from the tool. In some procedures, there may be several places of interest in the surgical site—the OCT control system can be configured (e.g., with appropriate programming of a control system processor) so that the OCT beam follows the tool's orientation, thus allowing the surgeon to direct the beam by adjusting the orientation of the tool. The OCT display changes to reflect the changed direction of the beam, providing the surgeon with optimal imaging of the surgical site.

Figure 9:
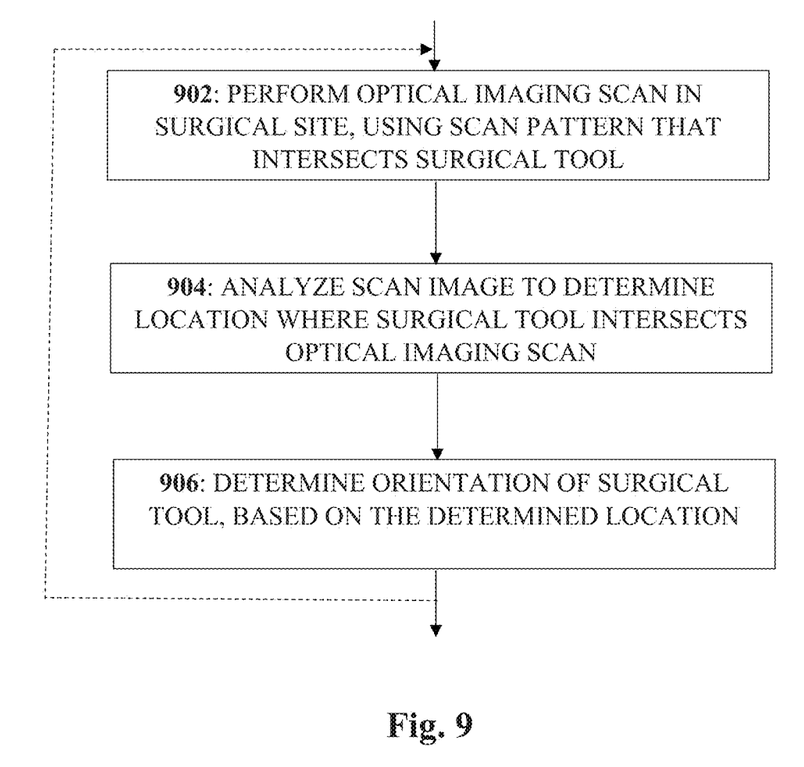
FIG. 9 is a flow chart illustrating an example method for determining the orientation of a surgical tool.

FIG. 9 is a flow chart illustrating an example method 900 of determining an orientation of a surgical tool during ophthalmic surgery, the illustrated method encompassing many of the example techniques described above. As shown at block 902, the illustrated method begins with performing an optical imaging scan in the surgical site, using a scan pattern that intersects the surgical tool and generating a scan image from the optical imaging scan. The detailed examples provided above were based on OCT imaging, but it will be appreciated that the disclosed techniques can be applied more generally, to other optical imaging techniques.

As shown at block 904, the method further comprises analyzing the scan image to determine a location in the scan image corresponding to where the surgical tool intersected the optical imaging scan. As discussed above, this may involve identifying a "gap" in the scan image, caused by the shadowing of the scan by the surgical tool. Typically, the contrast between this gap and the surrounding image data will be quite high, allowing for an accurate estimation of where the center of the surgical tool's shaft crosses the scan pattern.

As shown at block 906, the method further comprises determining an orientation of the surgical tool, based on the determined location. Several variations of this technique were described above. In some embodiments of the illustrated method, the scan pattern comprises an at least substantially closed pattern that surrounds an estimated position of a distal tip of the surgical tool. This scan pattern may be substantially continuous, in some embodiments, but may also consist of a series of discrete scans having separations smaller than a lateral dimension of a shaft of the surgical tool.

In some embodiments, the scan pattern has a center positioned at or near the estimated position of the distal tip of the surgical tool. In some of these embodiments, determining the orientation of the surgical tool comprises determining a tool orientation angle directly from the location in the scan image corresponding to where the surgical tool intersected the optical imaging scan. This may be done, for example, with a look-up table that relates portions of the scan image to corresponding angles, with respect to the center of the scan pattern.

In some embodiments, determining an orientation of the surgical tool comprises determining a first two-dimensional coordinate, for the location in the scan image corresponding to where the surgical tool intersected the optical imaging scan, and calculating an tool orientation angle based on the first two-dimensional coordinate and based on a second two-dimensional coordinate, where the second two-dimensional coordinate corresponds to the estimated position of the distal tip of the surgical tool.

In some embodiments, the scan pattern comprises first and second at least substantially closed patterns that each surround an estimated position of a distal tip of the surgical tool. In some of these embodiments, the scan image is analyzed to determine first and second locations in the scan image corresponding to where the surgical tool intersected the first and second at least substantially closed patterns of the optical imaging scan, respectively. The orientation of the surgical tool is then determined by determining an orientation angle of the surgical tool based on the determined first and second locations. In these embodiments, a precise estimate of the position of the surgical tool's tip is unnecessary, so long as the first and second closed patterns both surround the tip.

With some imaging techniques, including the OCT imaging discussed above, the optical imaging scan is an interferometric or confocal line scan that provides depth information along a path traced by the scan, such that the generated scan image comprises a representation of the depth information. In some of these embodiments, a height of a top surface of the surgical tool can be estimated, based on the generated scan image. Then, a three-dimensional orientation of the surgical tool can be determined, based on the estimated height and based on the location in the scan image corresponding to where the surgical tool intersected the optical imaging scan.

Of course, the performing, analyzing, and determining illustrated in FIG. 9 can be repeated multiple times, to track a changing orientation of the surgical tool over a period of time. In some embodiments, the determined orientation of the surgical tool can be used to adjust an angle of a subsequent optical imaging scan. In some of these and in some other embodiments, the determined orientation of the surgical tool can be used to adjust a display of the imaged surgical site.

Figure 10:
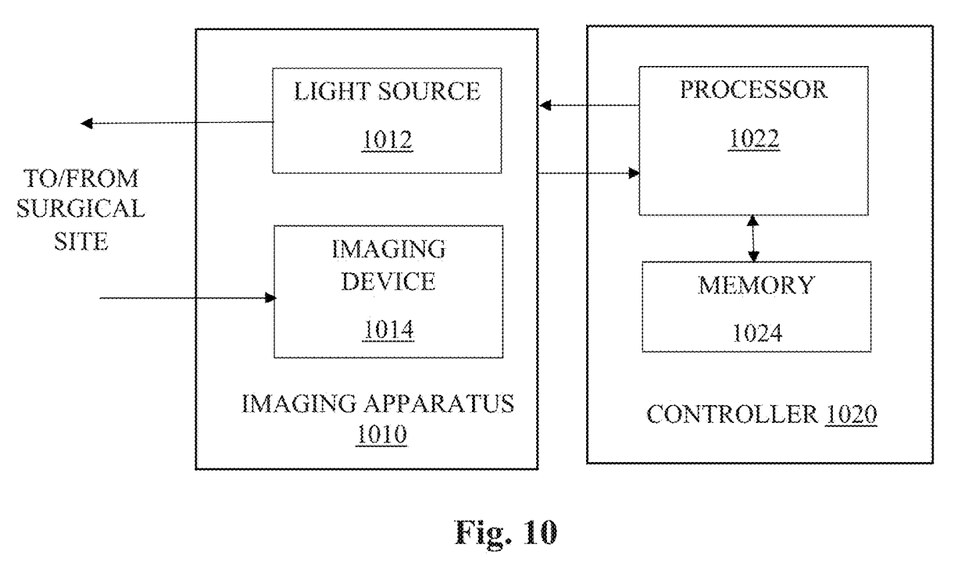
FIG. 10 is a block diagram illustrating an example system for determining the orientation of a surgical tool.

FIG. 10 is a schematic diagram illustrating components of a system for determining an orientation of a surgical tool during ophthalmic surgery. It will be appreciated that the system of FIG. 10, and variants of that system, may be implemented as part of the example tool tracking system illustrated in FIG. 1.

The system shown in FIG. 10 includes an optical imaging apparatus 1010 configured to perform optical imaging scans in the surgical site, the optical imaging apparatus in turn comprising a light source 1012 configured to introduce an imaging light into the surgical site and an imaging device 1014 configured to receive imaging light reflected from the surgical site and to generate a scan image from each optical imaging scan. The system further comprises a controller 1020 operatively coupled to the optical imaging apparatus 1010. In the illustrated embodiment, controller 1020 includes a processor 1022 and memory 1024, where memory 1024 includes an executable program for operating the system and provides storage for imaging data and other program data.

Controller 1020 is configured to, among other things, control the optical imaging apparatus to perform an optical imaging scan using a scan pattern configured to intersect the surgical tool and to generate a scan image from the optical imaging scan. Controller 1020 is further configured to analyze the scan image to determine a location in the scan image corresponding to where the surgical tool intersected the optical imaging scan, and determine an orientation of the surgical tool, based on the determined location. As discusses above, the optical imaging scan may be an optical coherence tomography (OCT) line scan.

The detailed operation of the controller 1020 may correspond to any of the variations of the method illustrated in FIG. 9, for example, and/or to any of the example techniques illustrated in FIG. 3 to FIG. 8, as described in detail above.

Several methods, devices, and systems for determining the orientation of a surgical tool have been described above and illustrated in the accompanying figures. It will be appreciated by persons of ordinary skill in the art that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A method of providing a tool angle feedback to an optical image scanning system to avoid shadowing from a surgical tool during ophthalmic surgery, the method comprising:
    performing an optical imaging scan in a surgical site, using a scanning beam in a scan pattern that intersects the surgical tool;
    generating a scan image from the optical imaging scan;
    analyzing the scan image to detect a boundary of a marker on the surgical tool and to analyze a shape of the marker on the surgical tool to determine a location in the scan image corresponding to where the surgical tool intersected the optical imaging scan;
    determining an orientation of the surgical tool based on the determined location;
    providing information describing the orientation of the surgical tool to the optical image scanning system;
    determining, by the optical image scanning system, a new angle of a subsequent scanning beam for a subsequent optical scan based on the orientation of the surgical tool, wherein the new angle of the subsequent scanning beam reduces a shadowing affect caused by the surgical tool; and
    adjusting an angle of the subsequent optical imaging scan to the new angle.

2. The method of claim 1, wherein the optical imaging scan is an optical coherence tomography (OCT) scan.

3. The method of claim 1, wherein the optical imaging scan is a confocal laser scan.

4. The method of claim 1, wherein the scan pattern comprises a closed pattern that surrounds an estimated position of a distal tip of the surgical tool.

5. The method of claim 4, wherein the scan pattern consists of a series of discrete scans having separations smaller than a lateral dimension of a shaft of the surgical tool.

6. The method of claim 4, wherein the scan pattern has a center positioned at the estimated position of the distal tip of the surgical tool, and wherein the determining the orientation of the surgical tool comprises determining a tool orientation angle directly from the location in the scan image corresponding to where the surgical tool intersected the optical imaging scan.

7. The method of claim 4, wherein determining the orientation of the surgical tool comprises determining a first two-dimensional coordinate for the location in the scan image corresponding to where the surgical tool intersected the optical imaging scan, and calculating a tool orientation angle based on the first two-dimensional coordinate and based on a second two-dimensional coordinate, the second two-dimensional coordinate corresponding to the estimated position of the distal tip of the surgical tool.

8. The method of claim 4, wherein the scan pattern comprises first and second closed patterns that each surround the estimated position of the distal tip of the surgical tool, wherein the method further comprises analyzing the scan image to determine first and second locations in the scan image corresponding to where the surgical tool intersected the first and second closed patterns of the optical imaging scan, respectively, and wherein determining the orientation of the surgical tool comprises determining an orientation angle of the surgical tool based on the determined first and second locations.

9. The method of claim 4, wherein the optical imaging scan is an interferometric or confocal scan that provides a depth information along a path traced by the optical imaging scan, such that the generated scan image comprises a representation of the depth information, and wherein determining the orientation of the surgical tool comprises estimating a height of a top surface of the surgical tool based on the generated scan image and determining a three-dimensional orientation of the surgical tool based on the estimated height and based on the location in the scan image corresponding to where the surgical tool intersected the optical imaging scan.

10. The method of claim 1, further comprising repeating said performing, analyzing, and determining to track a changing orientation of the surgical tool over a period of time.

11. The method of claim 1, further comprising adjusting a display of an imaged surgical site based on the determined orientation of the surgical tool.

12. A system to provide a tool angle feedback to avoid shadowing from a surgical tool during ophthalmic surgery, the system comprising:
    an optical imaging apparatus configured to emit imaging beams in a series of optical imaging scans in a surgical site, the optical imaging apparatus comprising:
        a light source configured to introduce an imaging light into the surgical site; and
        an imaging device configured to receive imaging light reflected from the surgical site and to generate a scan image from each of the series of optical imaging scans; and
    a controller operatively coupled to the optical imaging apparatus and configured to:
        control the optical imaging apparatus to perform the series of optical imaging scans using the imaging beams in a scan pattern configured to intersect the surgical tool and to generate the scan image from each of the series of optical imaging scans;
        analyze the scan image to detect a boundary of a marker on the surgical tool and to analyze a shape of the marker on the surgical tool to determine a location in the scan image corresponding to where the surgical tool intersected the series of optical imaging scans;
        determine an orientation of the surgical tool based on the determined location;
        provide information describing the orientation of the surgical tool to the optical image scanning apparatus;
        determine a new angle of a subsequent scanning beam for a subsequent optical scan based on the orientation of the surgical tool, wherein the new angle of the subsequent scanning beam reduces a shadowing affect caused by the surgical tool; and adjust an angle of the subsequent scanning beam of the subsequent optical imaging scan to the new angle.

13. The system of claim 12, wherein the series of optical imaging scans is an optical coherence tomography (OCT) scan.

14. The system of claim 12, wherein the series of optical imaging scans is a confocal laser scan.

15. The system of claim 12, wherein the scan pattern comprises a closed pattern that surrounds an estimated position of a distal tip of the surgical tool.

16. The system of claim 15, wherein the scan pattern consists of a series of discrete scans having separations smaller than a lateral dimension of a shaft of the surgical tool.

17. The system of claim 15, wherein the scan pattern has a center positioned at the estimated position of the distal tip of the surgical tool, and wherein the controller is configured to determine the orientation of the surgical tool by determining a tool orientation angle directly from the location in the scan image corresponding to where the surgical tool intersected the series of optical imaging scans.

18. The system of claim 15, wherein the controller is configured to determine the orientation of the surgical tool by determining a first two-dimensional coordinate for the location in the scan image corresponding to where the surgical tool intersected the series of optical imaging scans, and calculating a tool orientation angle based on the first two-dimensional coordinate and based on a second two-dimensional coordinate, the second two-dimensional coordinate corresponding to the estimated position of the distal tip of the surgical tool.

19. The system of claim 15, wherein the scan pattern comprises first and second closed patterns that each surround the estimated position of the distal tip of the surgical tool, and wherein the controller is configured to analyze the scan image to determine first and second locations in the scan image corresponding to where the surgical tool intersected the first and second closed patterns of the series of optical imaging scans, respectively, and to determine the orientation of the surgical tool comprises by determining an orientation angle of the surgical tool based on the determined first and second locations.

20. The system of claim 15, wherein the series of optical imaging scans is an interferometric line scan that provides a depth information along a path traced by the series of optical imaging scans, such that the generated scan image comprises a representation of the depth information, wherein determining the orientation of the surgical tool comprises estimating a height of a top surface of the surgical tool, based on the generated scan image, and wherein the controller is configured to determine a three-dimensional orientation of the surgical tool based on the estimated height and based on the location in the scan image corresponding to where the surgical tool intersected the series of optical imaging scans.

21. The system of claim 12, wherein the controller is configured to repeat said controlling, analyzing, and determining to track a changing orientation of the surgical tool over a period of time.

22. The system of claim 12, wherein the controller is further configured to adjust a display of an imaged surgical site based on the determined orientation of the surgical tool.

\* \* \* \* \*